(12) United States Patent
Elased et al.

(10) Patent No.: US 7,332,296 B2
(45) Date of Patent: Feb. 19, 2008

(54) SCREENING ASSAY FOR ENZYMES INVOLVED IN PATHOPHYSIOLOGY USING SELDI-TOF MASS SPECTROMETRY

(75) Inventors: Khalid M. Elased, Bellbrook, OH (US); Mariana Morris, Yellow Springs, OH (US)

(73) Assignee: Wright State University, Dayton, OH (US)

( * ) Notice: Subject to any disclaimer, the term of this patent is extended or adjusted under 35 U.S.C. 154(b) by 0 days.

(21) Appl. No.: 11/292,806

(22) Filed: Dec. 2, 2005

(65) Prior Publication Data

US 2006/0160167 A1 Jul. 20, 2006

Related U.S. Application Data

(60) Provisional application No. 60/632,223, filed on Dec. 2, 2004.

(51) Int. Cl.
*C12Q 1/37* (2006.01)
*G01N 24/00* (2006.01)
*G01N 1/00* (2006.01)

(52) U.S. Cl. .................. 435/24; 436/173; 436/174
(58) Field of Classification Search ................ None
See application file for complete search history.

(56) References Cited

U.S. PATENT DOCUMENTS

| | | | |
|---|---|---|---|
| 5,118,937 A | 6/1992 | Hillenkamp et al. | |
| 5,617,060 A | 4/1997 | Wilson et al. | |
| 6,225,047 B1 | 5/2001 | Hutchens et al. | |
| 6,579,719 B1 | 6/2003 | Hutchens et al. | |
| 6,811,969 B1 | 11/2004 | Hutchens et al. | |
| 6,844,165 B2 | 1/2005 | Hutchens et al. | |
| 6,881,586 B2 | 4/2005 | Hutchens et al. | |

OTHER PUBLICATIONS

Enzyme Nomenclature Supplement 10 (2004), NC-IUBMB website; http://www.chem.qmul.ac.uk/iubmb/enzyme/suypplements/sup2004/.*
Binder et al. Interrelationships Between the Renin Angiotensin System and Uteroplacental Blood Flow-A Recent Perspective; Reprod. Fertil. Dev., vol. 7 (1995) pp. 1437-1442.*
Xiao et al. Quantitation of Serum Prostate-Specific Membrane Antigen by a Novel Protein Biochip Immunosassay Discriminates Benign From Malignant Prostate Disease; Cancer Research, vol. 61 (2001) pp. 6029-6033.*
Caputo et al. Methods for On-Chip Protein Analysis; Analytical Biochemistry, vol. 321 (2003) pp. 116-124.*
Donaghue et al. A Novel Angiotensin-Converting Enzyme-Related Carboxypeptidase (ACE2) Converts Angiotensin I to Angiotensin 1-9; Circulation Research, vol. 87 (2000) pp. 1-9.*
Swedburg et al. Hormones Regulating Cardiovascular Function with Severe Congestive Heart Failure and Their Relation to Mortality; Circulation, vol. 82, No. 5 (1990) pp. 1730-1736.*

* cited by examiner

*Primary Examiner*—Jon Weber
*Assistant Examiner*—Paul Martin
(74) *Attorney, Agent, or Firm*—Foley & Lardner LLP

(57) ABSTRACT

The invention provides methods for quantifying enzymatic activity of an enzyme with a known substrate. The methods employ SELDI-TOF mass spectrometry, and are suitable, in particular, for assaying aspects of the renin-angiotensin system. The methods may be utilized to assess and/or monitor biological conditions associated with the renin-angiotensin system prior to the manifestation of known physiological and biomarkers for such conditions. The methods are suitable for analysis of pharmacological effectors of the renin-angiotensin system, and are particularly suitable for automation and high-throughput screening assay design.

12 Claims, 5 Drawing Sheets

SCREENING ASSAY FOR ENZYMES INVOLVED IN PATHOPHYSIOLOGY USING SELDI-TOF MASS SPECTROMETRY

RELATED APPLICATION

The present application claims priority under 35 U.S.C. §119 of U.S. Application Ser. No. 60/632,223 filed Dec. 2, 2004.

GOVERNMENT INTERESTS

The invention was funded, at least in part, by the federal government the NHLBI—grant number 5R01HL069319-03 (S)

BACKGROUND OF THE INVENTION

The present invention relates generally to the science and technologies of bio-processing. The invention is directed to a quantitative assay method comprising SELDI-TOF Mass Spectrometry to screen for, detect, measure and monitor enzymatic activity in biological samples. SELDI-TOF Mass Spectrometry is an increasingly popular bio-analytical method due in part to the development of techniques that avoid protein fragmentation during the process of volatization (e.g. desorption) and ionization. Other advantages of using SELDI-TOF Mass Spectrometry comprise the ability to identify proteins in a complex sample mixture with high resolution. The use of Mass Spectrometry for protein analysis is described in U.S. Pat. No. 5,118,937 (Hillenkamp et al.), U.S. Pat. No. 5,617,060 (Hutchens et al.) and WO 98/59360 (Hutchens and Yip). However, the present invention uniquely describes the use of SELDI-TOF Mass Spectrometry to accurately quantify enzymatic activity of enzymes with known substrates, or to evaluate effectors (i.e. activators or inhibitors) of such enzymes, directly in native biological samples (e.g. saliva, blood plasma, urine, spinal fluid, or any body fluid, cell or tissue preparations, surfactants).

There is a need for fast, accurate and physiologically relevant methods of analysis of enzymatic activity using unmodified (e.g. native, authentic, natural) substrates of enzymes present in crude biological samples, and, in particular, for methods permitting screening and monitoring of enzymatic biomarkers associated with pathological conditions such as, for example, those resulting from dysfunction of the renin-angiotensin system (RAS). There is also a need for efficiently identifying new therapeutic agents from libraries of compounds targeting such conditions.

SUMMARY OF THE INVENTION

Accordingly, the present invention addresses these needs by providing a bio-analytical method that detects specific products of an enzymatic reaction for which the substrate is known, in minute quantities of crude biological samples deposited on a protein chip (e.g., available from Ciphergen Biosystems, Calif.), which is thereafter read by SELDI-TOF Mass Spectrometry, for qualitative analysis and remarkably precise quantification of products of the enzymatic reaction.

Although the invention is not limited to specific advantages, it is a unique feature of the inventive method in that it provides for a means to quantitatively measure the physiologically relevant enzymatic activity in biological samples. Another advantage of the present methods includes the capability of conducting multiplex analysis, that is, measuring several enzymatic activities in the same sample simultaneously. A further advantage of the present invention comprises the need for a only minute quantity of a biological sample to perform the assay, the ability to scale up the assay, and the capability of processing a large number of samples in a very short amount of time and at a low cost. A significant advantage of the present methods is that they permit qualitative and quantitative analysis of enzymatic activity in native biological samples, reducing the labor and complexity associated with such analysis.

Accordingly, one embodiment of the present invention provides a method of quantifying enzymatic activity of an enzyme with a known substrate. The method comprises: a) obtaining a biological sample; b) adding at least one known substrate of an enzyme to the biological sample and incubating to generate enzymatic activity products, forming a mixture; c) loading the mixture onto a protein chip; d) washing to loaded chip to remove any unbound proteins and contaminants; e) reading the loaded chip using SELDI-TOF mass spectrometry; f) generating spectral data using commercially available software compatible for this purpose; g) analyzing the spectral data to identify the enzymatic activity products; and h) subjecting the spectral data to an algorithm that permits quantification of the enzymatic activity products.

Another embodiment of the present invention provides methods of assessing a biological condition by identifying and/or quantifying enzymatic products of an enzymatic system in a biological sample, wherein the enzymatic system is associated with the biological condition. The method comprises: a) obtaining the biological sample from an individual; b) adding a known substrate of an enzyme to the biological sample to form a mixture; c) loading the mixture onto a protein chip; d) washing the loaded chip to remove any unbound proteins and contaminants; e) reading the loaded chip using SELDI-TOF mass spectrometry; f) performing an analysis using commercially available software; g) identifying and/or quantifying enzymatic products; and h) assessing the biological condition by comparing the identification and quantity of enzymatic products from g) with a known or derived control standard for the biological condition.

In another embodiment, methods are provided of evaluating effectors of an enzyme in a native biological sample, wherein the enzyme has a known substrate. The methods comprise: a) obtaining a biological sample; b) incubating the biological sample with the known substrate of the enzyme, and an enzyme effector, resulting in a mixture; c) loading the mixture onto a protein chip; d) washing the loaded chip to remove any unbound proteins and contaminants; e) reading the loaded chip using SELDI-TOF mass spectrometry; f) generating spectral data and conducting a qualitative and/or quantitative analysis of the spectral data to determine a level of an enzymatic product; and g) comparing the determined level of an enzymatic product to a control level, wherein an increase in the level of an enzymatic product relative to the control indicates that the effector is an enzyme activator, and wherein a decrease in the level of the enzymatic product relative to the control indicates that the effector is an enzyme inhibitor.

Because of the small sample size requirement and ability to conduct the inventive methods with respect to more than one enzyme in parallel, the present inventive may be at least partially automated and incorporated in high throughput screening paradigms designed to screen agents for pharmacological efficacy in the renin-angiotensin system and the diseases associated therewith. Accordingly, the present invention provides high throughput screening assays for screening of agents to treat disorders associated with the renin-angiotensin system.

These and other features and advantages of the present invention will be more fully understood from the following detailed description of the invention taken with the accompanying drawings. The following figures are set forth to illustrate certain embodiments of the present invention, and should not be construed as limiting the invention as defined by the claims.

DETAILED DESCRIPTION OF THE INVENTION

Figure 1A:
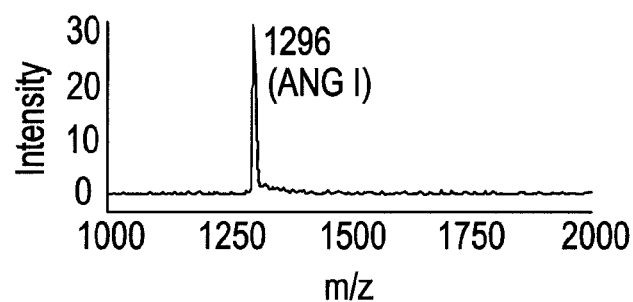
FIG. 1: Illustrates a SELDI-TOF analysis of ACE and renin activity in mouse plasma. Plasma (0.5 µl) was incubated with Ang I (1 µM) or AGT (4 µM) for 2 hours in the absence or presence of captopril (10 µM) and the generated peptides were analyzed with SELDI-TOF-MS. 1(A): Ang I; 1(B): Ang I+plasma; 1(C): Ang I+plasma+captopril; 1(D): AGT; 1(E): AGT+plasma; 1(F): AGT+plasma+captopril.

The conventional method for the identification and analysis of proteins uses 2 dimensional Poly Acrylamide Gel Electrophoresis (PAGE) followed by mass spectrometry. Although this method provides excellent resolution, it is time consuming, labor intensive and requires large amounts of sample, which hampers fast analysis of a large number of samples. Furthermore, multiple manipulations of proteins increases the risk for permanent denaturation, partial or total degradation, which are likely to negatively impact their function, for example catalytic in the case of enzymes.

Surface Enhanced Laser Desorption Ionization-Time of Flight (SELDI-TOF) Mass Spectroscopy is a novel approach that combines two powerful analytical techniques: chromatography and mass spectrometry. Proteins are retained on a ProteinChip© array which consists in a solid-phase chromatographic surface that has been modified in a manner such that it retains proteins based on their physio-chemical or biological properties. Biochemical chromatographic arrays are particularly well-suited to investigate specific molecular recognition mechanisms such as antibody-antigen or receptor-ligand interactions. Among other advantages, this method only requires minute sample volumes, in the micro liter order of magnitude, is compatible with spotting crude biological samples, and preserves the native structures of the proteins to be analyzed. After washing the arrays to eliminate excess of unbound molecules, salts or contaminants, and drying, a solution containing an Energy Absorbing Molecule is added to the ProteinChip® which is thereafter inserted into the ProteinChip® reader to measure the molecular weights of the bound proteins. The ProteinChip® reader is a Laser Desorption/Ionization Time of Flight mass spectrometer. A UV nitrogen laser source irradiates the molecules present in the samples, which causes their desorption/ionization as gaseous ions whose mass-to-charge ratio (m/z) is measured based on the velocity of each molecular ion through an ion chamber. An analog-to-digital converter linked to a personal computer processes the signals, and each detected protein shows as a peak on a spectrum. The height of the peaks and area-under-the curve permit quantification of each protein species detected in the sample.

The versatility of the SELDI-TOF Mass spectrometry technique has led to a broad range of applications in clinical, diagnostic and proteomics. However, the present inventors are unaware that this technique has ever been used to measure disease-associated modification of enzymatic activity.

Enzymes comprise molecules that reversibly and specifically bind to a variety of substrates to enable chemical reaction otherwise comprised under normal physiological conditions to occur. Because enzymes are proteins, their structure is very sensitive to a variety of environmental factors that influence the kinetics of the enzymatic equilibrium, and their function. The affinity between enzyme, substrate and/or cofactor, which largely depends on the conformational fit between these reagents, drives the enzymatic kinetics of the reaction. It is well-known in the art that modifying the conformational fit between an enzyme and its substrate, by changing the structure of either the enzyme or its substrate, for example by attaching a chromophore, changing the environment of the enzymatic reaction, or by genetically engineering the enzyme, may substantially modify the kinetics of the enzymatic reaction. Current experimental methods used to analyze proteolytic enzyme activity employ specially designed chromogenic substrates to enable measurement of activity by spectrophotometry. However, due to the use of a chromogenic substrate, the kinetics of the enzymatic reaction may not parallel that of the enzymatic reaction with natural substrates. Therefore, there may be a substantial discrepancy between the experimental and in vivo enzymatic activities.

Enzymes play a central role in the general metabolism of all living beings, and have therefore a vital physiological function. They often operate in concert thereby realizing enzymatic systems such as the renin-angiotensin system, or RAS (FIG. 3) which plays a crucial role in the regulation of blood pressure, cardiac function, and electrolyte balance. Angiotensin converting enzymes (ACE) are central actors of the Renin-Angiotensin System; they participate to the production of Angiotensin I (inactive) and II (vasoconstrictor). In addition to the circulating Renin-Angiotensin System, there is also tissue expression of this system in the brain, kidney, pancreas, and other organs. Enzymes of the Renin-Angiotensin System raise substantial clinical interest as biomarkers for pathological conditions such as hypertension, diabetes, or renal dysfunction.

Hypertension affects over 65 million people in the US, and is also acknowledged as being implicated in the development of cardiovascular disease, the top lethal condition in the US costing about $370 billion in total healthcare expenditures. Hypertension is also associated with a number of other pathological conditions such as diabetes, which affects an estimated 17 million Americans and costs about $98 billion in total healthcare expenditures in 1997, and renal disease which affects over 20 millions people and costs about $15 billion in healthcare expenditures.

Angiotensin Converting Enzyme (ACE) inhibitors are currently prescribed to control hypertension, to treat heart failure, to prevent heart attacks, as well as in diabetic kidney disease. Interestingly, more than two-thirds of high blood pressure patients are either untreated or on inadequate therapy, and about one half of the estimated diabetic population remains undiagnosed and is therefore not treated. It is widely acknowledged in the art that early diagnosis is critical for preventing onset or aggravation of secondary conditions such as cardiovascular disease or renal dysfunction.

Current assay methods for hypertension, cardiovascular disease or renal dysfunction require labor-intensive laboratory testing, such as spectrophotometry or radioimmunoassay (RIA), which hampers routine preventive detection or monitoring of these pathological conditions, and causes a significant number of individuals to remain undiagnosed or inappropriately treated.

The present invention provides an analytical method capable of quantitatively detecting abnormal enzymatic activity of the Renin-Angiotensin System indicating an increased risk to develop hypertension, cardiac or renal diseases. The analytical method may comprise a diagnostic assay which will detect the presence of products generated by the enzymatic reaction mediated by the Angiotensin Converting Enzyme 1 (ACE 1) or (ACE 2), or by renin in crude human or animal biological (e.g body fluid or tissue) samples. Ang II is a vasoconstrictor octapeptide well-known in the art, which is cleaved from Angiotensin I (inactive) by ACE 1-mediated proteolysis. It is therefore expected that an increase in ACE 1 activity, will result in an increase in Ang II measured by SELDI-TOF Mass Spectrometry, and indicate a high risk in the onset of hypertension. By providing a fast, accurate and sensitive analytical assay of the Renin-Angiotensin enzymatic system, the present invention is useful for early detection of, and therapeutic intervention in, hypertension which is commonly associated with diabetes as well as with the development of potentially fatal conditions such as cardiovascular or kidney disease.

The present inventive analytical assay is also useful to monitor the status of a pathological condition associated with a dysfunction of the Renin-Angiotensin System, such as hypertension, cardiac or renal disease. In one embodiment, biological samples from subjects treated for any of said conditions are assayed for the formation of products of the Renin-Angiotensin System using the combination of ProteinChip®-SELDI-TOF Mass Spectrometry. Angiotensin converting enzyme inhibitors (ACE Inhibitors) such as captopril (available under CAPOTEN®, from Bristol-Myers Squibb) are commonly administered to control hypertension, prevent cardiac diseases, as well as to lower protein excretion by the kidneys. Biological samples from subjects treated with captopril may be incubated with Ang I and then assessed for inhibition of Angiotensin II production. Angiotensin II levels above "normal" in such subjects indicate disease progression or inadequate drug dosage. Another embodiment of the present inventive methods provides a fast and accurate method for monitoring the effectiveness of a treatment regimen. This is expected to lower the risk for pathological complications and increase life expectancy in subjects being treated for hypertension, cardiovascular disease, or renal disease.

The present inventors have exploited the sensitivity and accuracy of the SELDI-TOF-MS/ProteinChip® technology, available from Ciphergen Biosystems of Fremont, Calif. This technology has previously been used to conduct on-chip enzymatic peptide sequencing, but, to the knowledge of the present inventors, has not been extensively applied to the measurement of enzymatic activity. ProteinChip arrays are derivatized with affinity matrices, which mirror the properties of conventional chromatographic media to capture peptides and proteins. One advantage of ProteinChip arrays is that a simple washing removes unbound peptides, residual salts or detergents that are present in crude biological extracts or buffers and which may interfere with mass analysis and reduce sensitivity. The present invention realizes the benefits associated with employing this sensitive and selective technology to develop novel methods for measuring proteolytic enzyme activities, specifically as related to the RAS.

Renin and ACE activity are currently known as biomarkers for certain disease states, including but not limited to hypertension, cardiac hypertrophy, diabetes, and renal dysfunction in general. The present invention provides assays for ACE1/ACE2 and renin, as representative of proteolytic enzymes which have defined substrates and enzyme products. In a broad embodiment, any enzymatic system having defined substrates and known enzyme products that is implicated or associated with a disease state may be suitably employed. The present methods are surprisingly capable of using endogenous peptide substrates with SELDI-TOF-MS analysis of products. The low fM sensitivity of SELDI-TOF permits the use of small sample volumes and substrate concentrations.

Accordingly, one embodiment of the present invention provides a method of quantifying enzymatic activity of an enzyme with a known substrate. The method comprises: a) obtaining a biological sample; b) adding at least one known substrate of an enzyme to the biological sample and incubating to generate enzymatic activity products, forming a mixture; c) loading the mixture onto a protein chip; d) washing to loaded chip to remove any unbound proteins and contaminants; e) reading the loaded chip using SELDI-TOF mass spectrometry; f) generating spectral data using commercially available software compatible for this purpose; g) analyzing the spectral data to identify the enzymatic activity products; and h) subjecting the spectral data to an algorithm that permits quantification of the enzymatic activity products. In a specific embodiment, the enzymatic activity is that of an enzyme associated with the renin-angiotensin system. In another specific embodiment, the substrate comprises renin or angiotensin I, and in further specific embodiments, the enzyme associated with the renin-angiotensin system is ACE1 or ACE2, and the enzymatic activity products comprise angiotensin 1 or angiotensin II. In an even more specific embodiment, the enzymatic activity products comprises angiotensin II. In certain embodiments where multiplex analysis is desired, the enzyme may comprise more than one enzyme having a known substrate, and quantification may be achieved in parallel.

Another embodiment provides methods of assessing a biological condition by identifying and/or quantifying enzymatic products of an enzymatic system in a biological sample, wherein the enzymatic system is associated with the biological condition. The method comprises: a) obtaining the biological sample from an individual; b) adding a known substrate of an enzyme to the biological sample to form a mixture; c) loading the mixture onto a protein chip; d) washing the loaded chip to remove any unbound proteins and contaminants; e) reading the loaded chip using SELDI-TOF mass spectrometry; f) performing an analysis using commercially available software; g) identifying and/or quantifying enzymatic products; and h) assessing the biological condition by comparing the identification and quantity of enzymatic products from g) with a known or derived control standard for the biological condition. According to one aspect of the inventive method, assessing comprises monitoring and a biological condition may be monitored, for example, over the course of treatment. In a specific embodiment, the enzymatic system comprises the renin-angiotensin system. In another specific embodiment, the biological sample comprises plasma separated from a blood sample obtained from an individual. In one embodiment, the protein chip comprises a weak cation-exchange protein chip, such as ProteinChip® (WCX2). Spectral analysis may be performed by using a commercially available software developed for this purpose (e.g. version 3.1 Ciphergen Biosystems). Quantifying the enzymatic products may be accomplished by any algorithm known by persons of ordinary skill in the art as suitable for that purpose. In particular embodiments, quantification of the enzymatic products is achieved via using peak height intensity and/or area-under-the-curve calculations.

According to a specific embodiment of the present inventive methods, the biological condition being assessed/monitored comprises a biological condition associated with the enzymatic system being subject to analysis. In a very specific embodiment, the biological condition comprises on or more of: hypertension, arterial disease, cardiac hypertrophy, heart failure, and diabetic renal disease. In certain embodiments it may be desirable to analyze the enzymatic activity in a native tissue. The tissue sample typically is homogenized prior to incubation with the known substrate.

In a further embodiment, methods are provided of evaluating effectors of an enzyme in a native biological sample, wherein the enzyme has a known substrate. The methods comprise: a) obtaining a biological sample; b) incubating the biological sample with the known substrate of the enzyme, and an enzyme effector, resulting in a mixture; c) loading the mixture onto a protein chip; d) washing the loaded chip to remove any unbound proteins and contaminants; e) reading the loaded chip using SELDI-TOF mass spectrometry; f) generating spectral data and conducting a qualitative and/or quantitative analysis of the spectral data to determine a level of an enzymatic product; and g) comparing the determined level of an enzymatic product to a control level, wherein an increase in the level of an enzymatic product relative to the control indicates that the effector is an enzyme activator, and wherein a decrease in the level of the enzymatic product relative to the control indicates that the effector is an enzyme inhibitor. In a specific embodiment, the enzyme comprises ACE1 and/or ACE2 and the known substrate comprises renin and/or angiotensin I, and/or angiotensinogen. According to another specific embodiment, the enzymatic product comprises Angiotensin II.

The present inventive methods may be used to determine whether an individual has an increased risk of developing diseases associated with an enzymatic cascade or system, and, in particular embodiments, the Renin-Angiotensin System. One may identify and quantify enzymatic products of the system in a biological sample derived from an individual, and compare it to a control measurement that is either a standard population-based control, or a control derived from the individual themselves, or some other suitable control or base level. Increased or decreased levels of the angiotensin II enzymatic product, for example, may suggest that an individual is at greater risk of developing disorders associated with dysfunction of the renal-angiotensin system at a point in the progression of the disease prior to the manifestation of conventional physical and biomarkers for the disorder.

Because of the small sample size requirement and ability to conduct the inventive methods with respect to more than one enzyme in parallel, the present inventive may be at least partially automated and incorporated in high throughput screening paradigms designed to screen agents for pharmacological efficacy in the renin-angiotensin system and the diseases associated therewith. Accordingly, the present invention provides high throughput screening assays for screening of agents to treat disorders associated with the renin-angiotensin system.

The examples provided below are intended to illustrate certain embodiments of the present invention and should not be construed as limiting the scope of the invention as defined by the recitation of the claims.

EXAMPLES

Figure 1B:
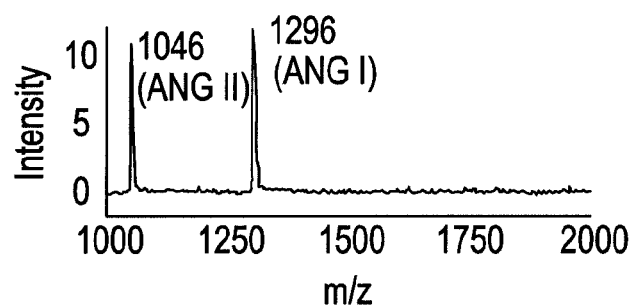
Figure 1C:
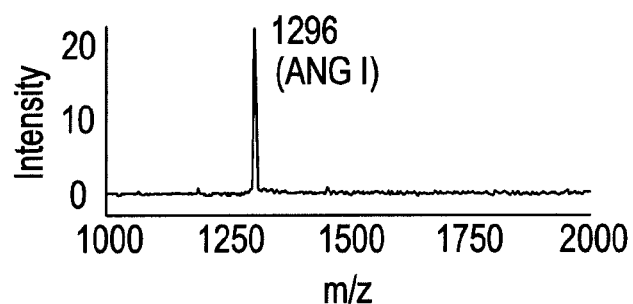
Figure 1D:
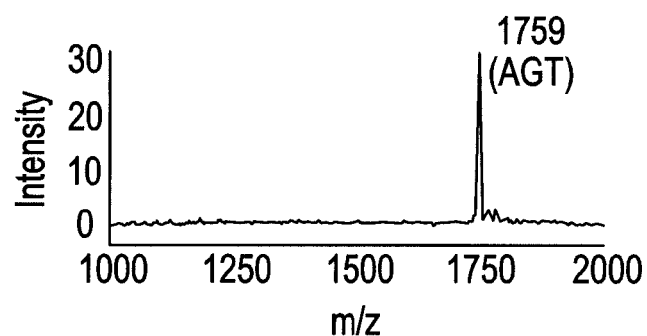
Figure 1E:
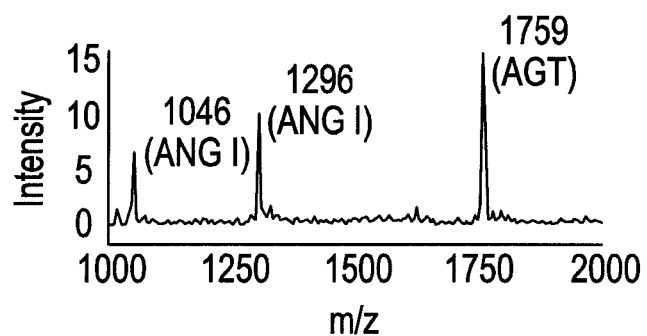
Figure 1F:
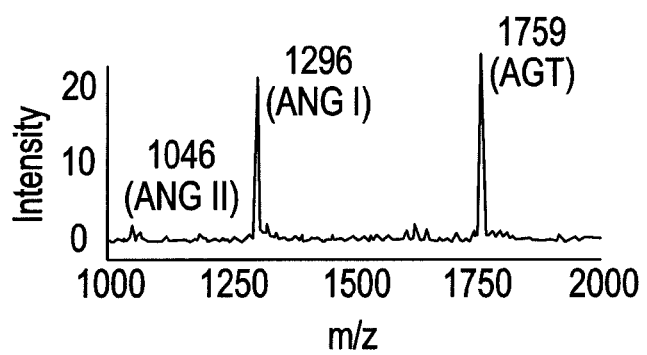
Figure 3:
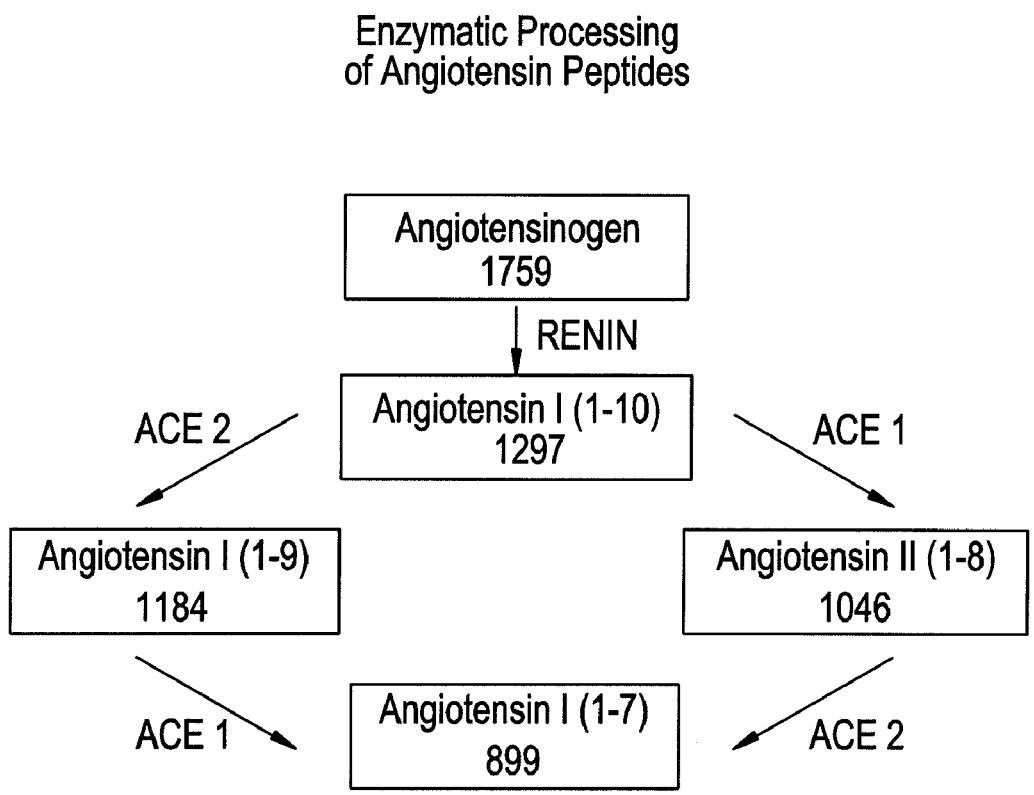
FIG. 3: Schematically illustrates the enzymatic processing of angiotensin peptides.

The first consideration in method protocol design is the enzymatic cascade of the Renin-Angiotensin System (see FIG. 3). Summarily, renin catalyzes the conversion of angiotensinogen (AGT) to angiotensin I (AngI), which is followed by the action of ACE 1, which catalyzes the cleavage of the C-terminal dipeptide from Ang I to produce Ang II. ACE2, a homologue of ACE1 which was recently cloned, cleaves a single amino acid from Ang I to generate Ang (1-9)(m/z, 1183) and from Ang II to generate Ang (1-7)(m/z,800). For measurement of enzyme activities, substrates (Ang II or AGT) were incubated with plasma or tissue extracts and the peptide products were measured using SELDI-TOF MS. For ACE activity, plasma (0.5-2.5 µl) or tissue extracts (1 µg protein) were incubated in 50 µl MES buffer (50 mM, pH 6.7) containing 2 mM PMSF and varying concentrations of Ang I(0.1-10 µM) at 37° C. One µl of the reaction mixture was spotted onto ProteinChip arrays and analyzed as previously described in Cool, D. R. & Hardiman, A., "C-Terminal sequencing of peptide hormones using carboxypeptidase Y and SELDI-TOF mass spectrometry" *Biotechniques* 36, 32-34 (2004), incorporated herein by reference. Briefly, 1 µl of the reaction mixtures were spotted onto ProteinChip WCX2 (a weak cation exchange chip), and incubated for 15 minutes in a humidified chamber at 37° C. Nonbound proteins, salts and other contaminants were washed from the chips with 5 µl of dionized water, three times. Enzymatic reactions were terminated by the addition of 1 µl of freshly prepared saturated matrix (α-cyano-4-hydroxycinnamic acid in 50% acetonitrile (v/v), containing 0.1% trifluoroacetic acid) and chips were dried at room temperature for ten minutes. Spectral analysis was performed with proprietary software (version 3.1, Ciphergen Biosystems). The source and detector voltages were 20000 and 1800V, respectively. Peptides were analyzed with a spot protocol that analyzes 13 different areas in each spot. Spots were warmed initially with 2 laser shots at 155 followed with 91 laser hits at 145 and sensitivity of 10. FIG. 1 shows the mass spectra of substrates and enzyme products after incubation of either Ang I or AGT with 0.5 µl plasma in the absence or presence of ACE1 inhibitor. Plasma ACE1 converted Ang I (Ang 1-10; 1296.5 m/z) to Ang II (Ang 1-8; 1046.3 m/z) as expected, by cleavage of the C-terminal His-Leu dipeptide (FIG. 1B). ACE activity was blocked by ACE1 inhibitor captopril (10 μM) (FIG. 1C) and by the chelating agents 10 mM EDTA and 0.44 mM 1, 10 phenanthroline (data not shown). The blockade by captopril, EDTA and 1, 10 phenanthroline indicates that the cleavage products were not produced by nonspecific degradation of Ang I, but rather via zinc metalloproteases, as disclosed in Tipnis, S. R. et al. "A human homolog of angiotensin-converting enzyme, Cloning and functional expression as a captopril-insensitive carboxypeptidase" J. Biol. Chem. 275, 33238-33243 (2000), the full disclosure of which is incorporated herein by this reference. A similar MS protocol was applied to measurement of renin activity. In this case, the renin substrate AGT (Ang 1-14), m/z) (0.1-5 μM) was used as substrate. Plasma incubated with AGT (1759, m/z) results in peptides with m/z that matched Ang 1 and Ang II (FIG. 1E). This is related to sequential effects of renin and ACE1. Captopril had no effect on renin activity, but as expected blocked ACE1 and increased Ang II levels (FIG. 1F).

Another advantage of the assay is the ability to multiplex, e.g. to screen for ACE1 and ACE2 in the same sample. It is well documented that ACE2 cleaves one amino acid from Ang II to produce Ang (1-7) (see Vickers, C. et al. "Hydrolysis of biological peptides by human angiotensin-converting enzyme-related carboxypeptidase," Biol. Chem. 277 14838-14843 (2002), and Tipnis, S. R. et al. "A human homolog of angiotensin-converting enzyme. Cloning and functional expression as a captopril-insensitive carboxypeptidase," J. Biol. Chem. 275, 33238-33243 (2000), both disclosures of which are incorporated herein by this reference. This was verified when kidney extracts (a known source of ACE2, see Vickers and Tipnis, supra) were incubated with Ang II. A peak with m/z of 899, corresponding to Ang (1-7), was generated, providing evidence of renal ACE2 activity (data not shown). The presence of ACE1 and absence of ACE2 in plasma was verified using this method (FIG. 1C).

Figure 2A:
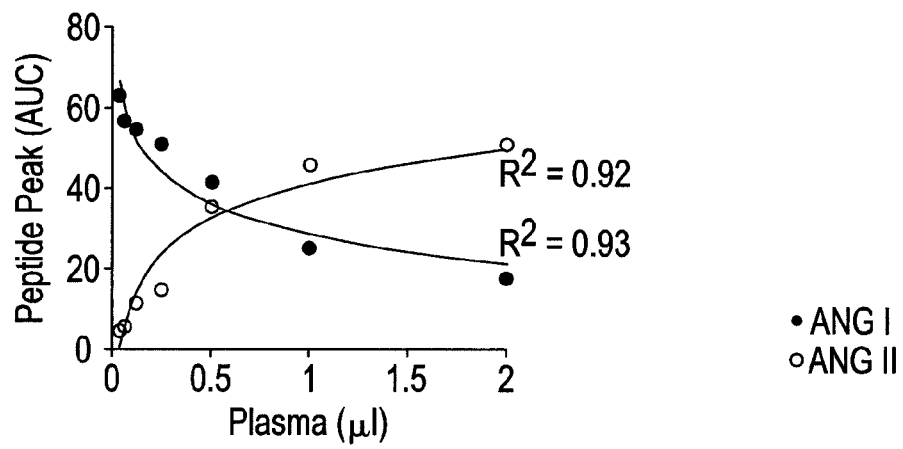
FIG. 2(A): Illustrates the relationship between plasma concentration and formation of Ang I and disappearance of Ang II. Ang I (1 µM) was incubated with variable amounts of mouse plasma for two hours. Generated peptides were analyzed with SELDI-TOF MS and quantified by area under the curve calculations.
Figure 2B:
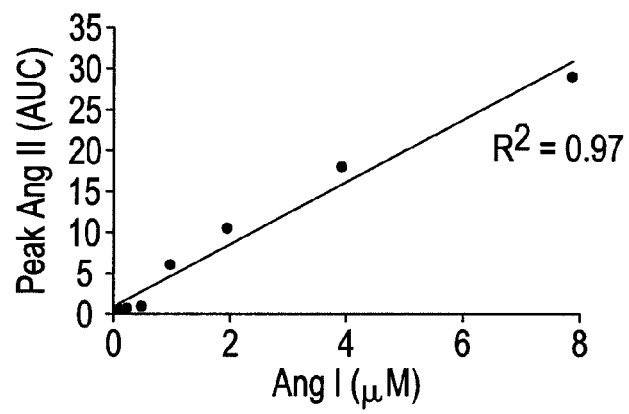
FIG. 2(B): Illustrates the relationship between the substrate, Ang I, and the product, Ang. II. Plasma (0.5 µl) was incubated for two hours with different concentrations of Ang I. Generated peptides were analyzed with SELDI-TOF-MS and quantified by area under the curve calculations.
Figure 2C:
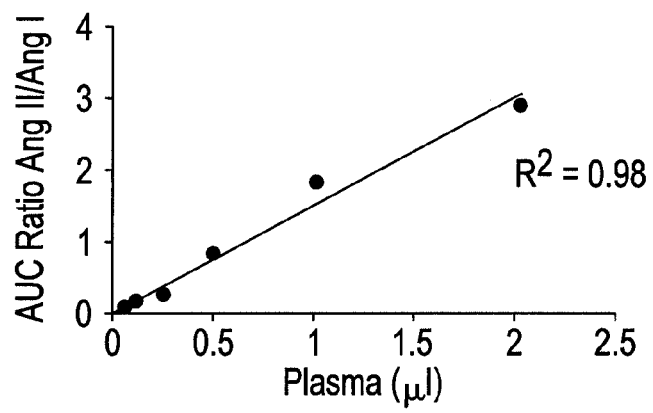
FIG. 2(C): Illustrates the relationship between plasma and the Ang II/Ang I ratio. Ang I (1 µM) was incubated with variable amount of plasma for two hours. Generated peptides were analyzed with SELDI-TOF-MS.

A major hurdle in comparative proteomics is identification and subsequent quantification of target peptides and proteins. The traditional method for MS quantification is to compare the unlabeled peptide to an internal standard that is chemically identical, except for inclusion of stable heavy isotopes. New approaches for MS quantification have been developed (see Venable, J. D. & Yates, J. R., III Impact of ion trap tandem mass spectra variability on the identification of peptides. Anal. Chem. 76, 2928-2937 (2004), incorporated fully herein by this reference), and include the use of relative intensity of peak height ratio of products to substrate. We used peak height intensity and area under the curve (AUC) as parameters for quantification of substrate and enzyme products. Although experimental conditions can affect mass spectral patterns, the technique is remarkably reproducible. The lack of background noise is clearly evident in the MS chromatograms (FIG. 1). The method benefited from the use of short incubation times and inclusion of a protease inhibitor, PMSF, in order to reduce nonspecific degradation of peptides. There is a good correlation between disappearance of the substrate, Ang I, and generation of product, Ang II and plasma concentrations (FIG. 2(A), $R^2=0.92$). FIG. 2(B) shows the correlation between the substrate (Ang I) and generation of Ang II ($R^2=0.97$). As expected there was a relationship between the peptide peak intensity and laser intensity. When laser intensities were compared, there was a higher Ang II peak intensity at 150 than at 140, 66±1.8 vs 29±5.5 (n=7). When the ratio of the peptide peaks (Ang I/Ang II) is used as the experimental index, no differences are noted between the low and high laser intensity (0.71±0.02; vs 0.70±0.03, low vs high laser intensity). There is also a linear relationship between Ang 1/Ang II ratio and plasma concentration (FIG. 2(C), $R^2=0.98$). This verifies the utility and the reproducibility of the method and demonstrates that the peptide ratio provides data which is independent of the laser settings or the substrate/enzyme concentrations.

Table 1 illustrates the enzymatic processing of peptides of the renin angiotensin system (RAS). The number indicates the molecular weight of the cleaved peptides. The method has been developed for assay of renin, ACE1 and ACE2, but could be applied to other enzymes.

Figure 4:
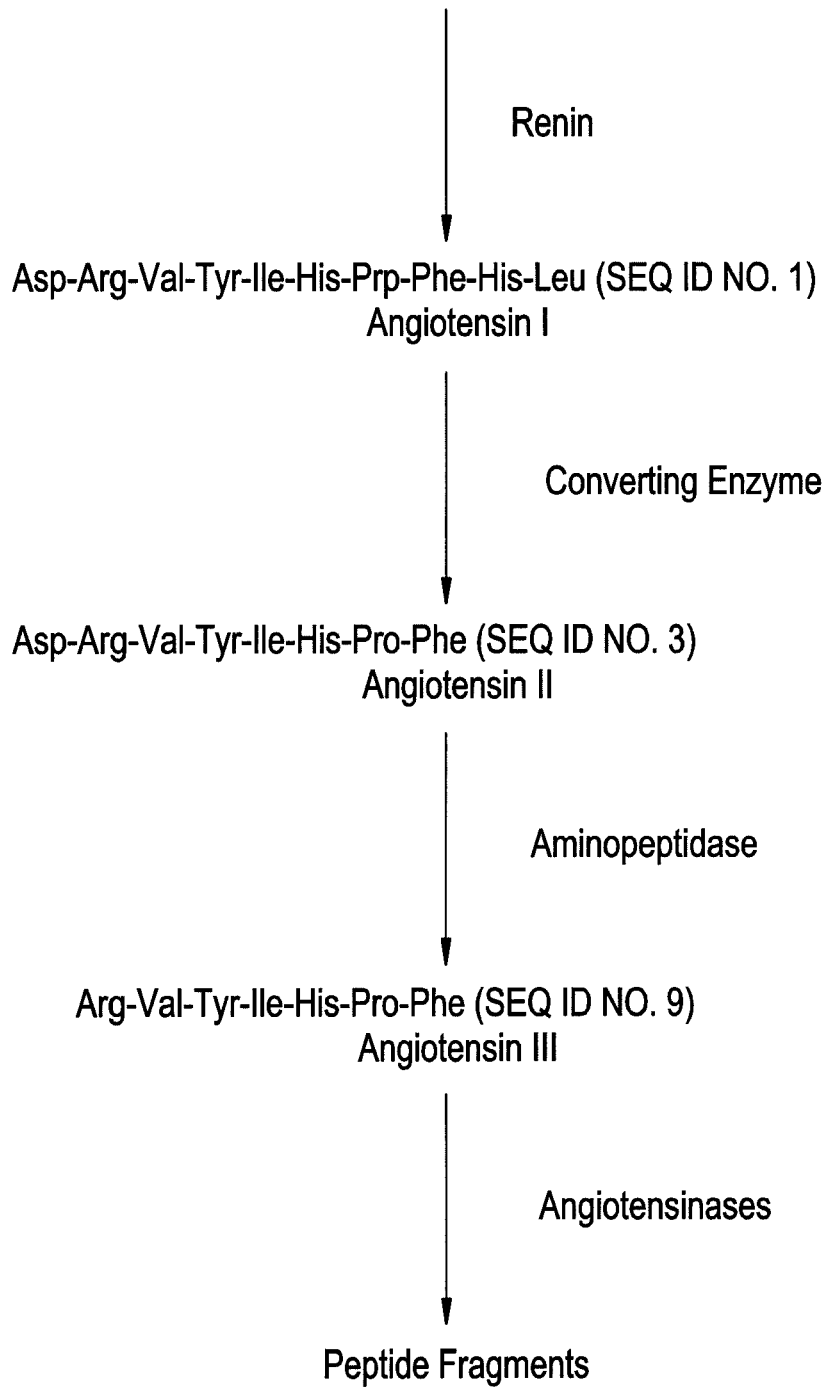
FIG. 4: Illustrates the chemistry of the rennin-angiotensin system, and the amino acid sequence of the amino terminus of human angiotensinogen is shown, with R being the remainder of the molecule. (SEQ ID NOS 8, 1, 3 & 9).

The RAS plays a crucial role in regulation of blood pressure, cardiac function and electrolyte balance. Renin acts upon the precursor substrate angiotensinogen to release the inactive decapeptide Angiotensin I (Ang I). Angiotensin converting enzyme (ACE1) cleaves off two amino acids from Ang I to form the vasoconstrictor octapeptide, angiotensin II (Ang II) (see FIG. 4). There is much interest in the use of plasma renin and ACE as markers for cardiovascular disorders. The typical methods of quantifying angiotensin peptides and related enzyme activity are spectrophotometry and radioimmunoassay (RIA). These methods have downsides related to the requirement for specific antisera, use of artificial substrates and a large sample volume. In the present study a novel method using natural substrates, based on Surface Enhanced Laser Desorption/Ionization Mass Spectrometry (SELDI-TOF-MS) is provided and optimized for assay of plasma renin and ACE activity.

Plasma or tissue extracts are incubated with either renin substrate (1759, m/z) or Ang I (1297, m/z) and generated peptides are measured on ProteinChip® Arrays using Ciphergen ProteinChips® Reader. Results demonstrate the formation of peaks corresponding to Ang I (1296, m/z) and Ang II (1046, M/Z) which indicates renin and ACE1 enzymatic activity, respectively. ACE2 activity was demonstrated by the formation of peaks corresponding to (1184, m/z) and or (899, m/z).

TABLE 1

Angiotensin related peptides generated by digestion of Ang I with Carboxypeptidase Y (CPY)

| Amino Acid Sequence | Molecular Weight | Name | |
|---|---|---|---|
| DRVYIHPFHL | 1297 | Ang I (1-10) | Angiotensin I |
| DRVYIHPFH | 1184 | Ang (1-9) | |
| DRVYIHPF | 1047 | Ang I (1-8) | Angiotensin II |
| DRVYIHP | 900 | Ang I (1-7) | |
| DRVYIH | 803 | Ang I (1-6) | |
| DRVYI | 667 | Ang I (1-5) | |
| DRVY | 554 | Ang I (1-4) | |

CPY was used to prove the concept of using MS to detect enzymatic sequencing of Ang I. Sequential cleavage of one amino acid from the c terminal of Ang I and the peptides formed was possible to be monitored using SELDI-TOF-MS.

In summary, the present invention provides novel methods for measurement of proteolytic enzyme activities. Using a SELDI-TOF MS approach, a rapid and sensitive method for assay of ACE and renin using endogenous peptide substrates is provided. The advantages of the method include, but are not limited to: 1) high sensitivity, allowing measurement in less than 1 μl plasma, 2) applicability for time course studies in animals and humans, 3) utility as a prototype for other enzyme assays wherein an enzyme has at least one known substrate, and 4) utility in high throughput system designs for testing drugs that affect the RAS.

What is claimed is:

1. A method of quantifying the enzymatic activity of at least one enzyme selected from the group consisting of renin, ACE1 and ACE2 with a known substrate, the method comprising:
   a) obtaining a biological sample comprising said at least one enzyme;
   b) adding at least one known substrate of said at least one enzyme to the biological sample and incubating to generate enzymatic activity products in a mixture;
   c) loading the mixture onto a protein chip to produce a loaded chip;
   d) washing the loaded chip to remove any unbound proteins and contaminants;
   e) reading the loaded chip using SELDI-TOF mass spectrometry;
   f) generating spectral data using commercially available software compatible for this purpose;
   g) analyzing the spectral data to identify the enzymatic activity products; and
   h) subjecting the spectral data to an algorithm that permits quantification of the enzymatic activity products.

2. The method according to claim 1, wherein the algorithm comprises an area-under-the-curve and/or peak height intensity calculations.

3. The method according to claim 1, wherein the known substrate comprises angiotensinogen, angiotensin I, angiotensin II, or Ang(1-7).

4. The method according to claim 1, wherein said at least one enzyme is ACE1 or ACE2.

5. The method according to claim 1, wherein the enzymatic activity products comprise angiotensin I or angiotensin II.

6. The method according to claim 5, wherein the enzymatic activity products comprises angiotensin II.

7. The method according to claim 1, wherein the at least one enzyme comprises more than one enzyme and quantification is achieved in parallel for each of the more than one enzymes.

8. A method for determining whether an individual has an increased risk of developing diseases associated with the Renin-Angiotensin System, the method comprising: quantifying angiotensin II according to the method recited in claim 5 and comparing the quantification of the angiotension II levels to a standard.

9. The method of claim 1, wherein said substrate is not labeled.

10. The method of claim 1, wherein said biological sample has a volume of 0.5 to 2.5 µl or less.

11. The method of claim 1, wherein the peak height ratio of products to substrate is measured.

12. The method of claim 1, wherein said substrate and said biological sample are incubated in the presence of PMSF.

* * * * *